US012045894B2

(12) United States Patent
Poteet, III et al.

(10) Patent No.: US 12,045,894 B2
(45) Date of Patent: *Jul. 23, 2024

(54) MACHINE LEARNING MODEL FOR PREDICTING HEALTH PLANS BASED ON MISSING INPUT DATA

(71) Applicant: CERNER INNOVATION, INC., Kansas City, MO (US)

(72) Inventors: James L. Poteet, III, Overland Park, KS (US); Raymond G. Delano, III, Leawood, KS (US); Julie Ann Jensen, Olathe, KS (US)

(73) Assignee: CERNER INNOVATION, INC., Kansas City, MO (US)

(*) Notice: Subject to any disclaimer, the term of this patent is extended or adjusted under 35 U.S.C. 154(b) by 0 days.

This patent is subject to a terminal disclaimer.

(21) Appl. No.: 18/235,492

(22) Filed: Aug. 18, 2023

(65) Prior Publication Data

US 2023/0394588 A1 Dec. 7, 2023

Related U.S. Application Data

(62) Division of application No. 16/812,535, filed on Mar. 9, 2020, now Pat. No. 11,763,390.

(Continued)

(51) Int. Cl.
G06Q 40/08 (2012.01)
G06F 18/213 (2023.01)
G06N 20/00 (2019.01)
G06Q 20/40 (2012.01)
G16H 10/60 (2018.01)

(52) U.S. Cl.
CPC ........... *G06Q 40/08* (2013.01); *G06F 18/213* (2023.01); *G06N 20/00* (2019.01); *G06Q 20/401* (2013.01); *G16H 10/60* (2018.01)

(58) Field of Classification Search
CPC .............................. G06Q 40/08; G06N 20/00
See application file for complete search history.

(56) References Cited

U.S. PATENT DOCUMENTS 7,392,237 B2 6/2008 Pratt
7,580,831 B2 8/2009 Haskell et al.
(Continued)

*Primary Examiner* — Edward Chang
(74) *Attorney, Agent, or Firm* — Kraguljac Law Group, LLC

(57) ABSTRACT

Methods, computer systems, and computer storage media are provided for utilizing machine learning to predict health plans. A machine learning model is trained to predict valid combinations of employer-payer-health plan in response to one or more missing identifiers based on transaction data from electronic data interchange (EDI) insurance transactions that include valid combinations of employer identifier, payer identifier, and health plan identifier. In response to a request to identify a valid combination based on at least one missing identifier, at least one known identifier corresponding to an employer name, a payer name, or a health plan name is inputted and work location data associated with a patient. The machine learning model generates and displays on a user interface, a predicted set of one or more valid combinations of employer-payer-health plans that correspond to the one known identifier and the work location information that is inputted.

20 Claims, 4 Drawing Sheets

Related U.S. Application Data

(60) Provisional application No. 62/955,590, filed on Dec. 31, 2019.

(56) References Cited

U.S. PATENT DOCUMENTS

| | | |
|---|---|---|
| 7,970,629 B2 | 6/2011 | Christen |
| 8,751,250 B2 | 6/2014 | Lutzen et al. |
| 9,721,315 B2 | 8/2017 | Christen |
| 2016/0063636 A1 | 3/2016 | Feimster et al. |
| 2019/0080416 A1* | 3/2019 | Smith .................... G06Q 40/08 |
| 2019/0095822 A1 | 3/2019 | Rugel et al. |

* cited by examiner

MACHINE LEARNING MODEL FOR PREDICTING HEALTH PLANS BASED ON MISSING INPUT DATA

CROSS REFERENCE TO RELATED APPLICATIONS

This disclosure claims benefit of U.S. patent application Ser. No. 16/812,535 filed Mar. 9, 2020, titled "Intelligently Linking Payer/Health Plan Combinations To Specific Employers", inventors: James L. POTEET, III, Raymond G. DELANO, III and Julie Ann JENSEN; which claims benefit of U.S. patent application Ser. No. "62/955,590" filed Dec. 31, 2019, titled "Intelligently Linking Payer/Health Plan Combinations To Specific Employers", inventors: James L. POTEET, III, Raymond G. DELANO, III and Julie Ann JENSEN; and assigned to the present assignee, which all incorporated by reference herein in their entirety.

BACKGROUND

Health care providers are dependent on accurate insurance information to ensure medical claims are correctly generated, matched and processed with medical plan data contained in electronic databases. Often patient insurance eligibility and health care claims are generated incorrectly and/or transmitted to the wrong payer or health plan, resulting in errors or denied claims. This situation may happen if the health plan on the insurance card cannot be matched to a health plan in the electronic health record system (EHR). Or, perhaps the health plan was built in the EHR using a slightly different name or is abbreviated or confused with or similarly named plan. Similar situations may arise if the patient is from a different state or locality and the provider organization has not built a particular health plan in the EHR. Sometimes, the health insurance card is scanned correctly but still manually matched to the wrong health plan and/or the electronic routing is configured incorrectly. In each of these scenarios, the electronic transactions are performed incorrectly and thus requiring corrective actions and repeating the transactions, which uses more computing system resources and processing time.

BRIEF SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present system relate to improving the technical field of systematically predicting payer/health plan combinations of data records with a machine learning model for situations where an insurance card is not presented or the card does not contain requested data (e.g., some identifiers are missing). Thus, the machine learning model makes predictions when initial input data is missing. In some embodiments, the system relates to utilizing machine learning to verify payers and/or health plans. More particularly, the present invention utilizes HIPAA transactions to train a machine learning model to intelligently link payers and/or health plans to specific employers. Initially, transaction data is received from electronic data interchange (EDI) insurance transactions. The transaction data comprises data corresponding to a plurality of employers, a plurality of payers, and a plurality of health plans provided by the plurality of payers. A machine learning model is trained with the transaction data to build a mapping of the plurality of employers, the plurality of payers contracted with each employer of the plurality of employers, and the plurality of health plans provided by the plurality of payers for each employer of the plurality of employers. The machine learning model is configured to generate and display on a display, a predicted set of one or more payer-health plan combinations that are valid with an employer identifier that corresponds to an inputted employer and work location data.

BRIEF DESCRIPTION OF THE SEVERAL VIEWS OF THE DRAWINGS

The present invention is described in detail below with reference to the attached drawing figures, wherein.

DETAILED DESCRIPTION

Figure 1:
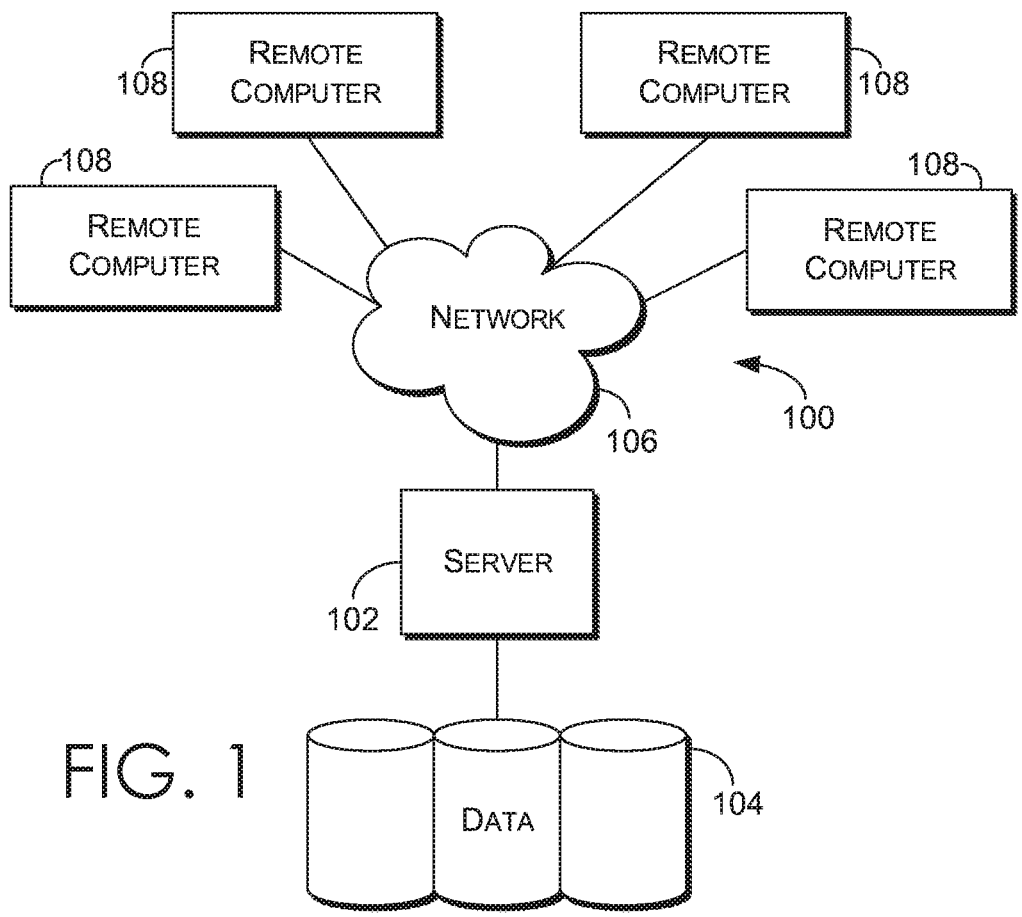
FIG. 1 is a block diagram of an exemplary computing environment suitable for use in implementing the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

As noted in the Background, health care providers are dependent on accurate insurance information to ensure medical claims are correctly generated, matched and processed with medical plan data contained in electronic databases. Often, due to incorrect data, patient insurance eligibility and health care claims are generated incorrectly and/or sent to the wrong payer or health plan, resulting in denied claims. For example, if the health plan on the insurance card cannot be matched to a health plan in the electronic health record system, the claim may be denied. In another example, if the health plan was built in the EHR using a slightly different name or is abbreviated or confused with or similarly named plan, the claim may be denied. The claim may also be denied if the patient is from a different state or locality and the provider organization has not built a particular health plan in the EHR. Even if the health insurance card is scanned correctly, it may be manually matched to the wrong health plan and/or the electronic routing is configured incorrectly, and the claim may be denied. In each of these scenarios, additional corrective actions are performed, and previous transactions are repeated, which uses more computing system resources and processing time.

Embodiments of the present invention relate to systematically predicting payer-health plan combinations from data records with a machine learning model for situations where an insurance card is not presented, is presented but does not include one or more identifiers, or otherwise identification data is missing. Thus, the machine learning model makes health plan predictions when initial input data is missing. In one embodiment, the system implements a machine learning model to verify payers and/or health plans. More particularly, the present invention utilizes HIPAA transactions to train a machine learning model to intelligently link payers and/or health plans to specific employers. Initially, transaction data is received from EDI insurance transactions. The transaction data comprises data corresponding to a plurality of employers, a plurality of payers, and a plurality of health plans provided by the plurality of payers. A machine learning model is trained with the transaction data to build a mapping of the plurality of employers, the plurality of payers contracted with each employer of the plurality of employers, and the plurality of health plans provided by the plurality of payers for each employer of the plurality of employers. The machine learning model can be utilized to verify the scan data is mapped in accordance with the mapping.

Embodiments of the present invention ensure medical claim data is accurately generated. Embodiments of the present invention provide validated insurance plans by utilizing machine learning techniques which may increase our confidence of health care providers when submitting medical claims to a third party (e.g., remote destination) so that the submitted medical claim data correctly matches data records maintained by the third party for approval. Embodiments of the present invention may provide health care providers additional benefits, such as: a) reduce the need for an extensive local reference build in the electronic health record system; b) reduce the time to complete a local payer and health plan build; c) reduce errors associated with picking the wrong payer or health plan; d) reduce errors associated with routing the correct payer and plan details to the wrong payer; e) provide faster, more accurate, and efficient patient registration with less manual data entry; f) provide a list of valid payer/health plans by employer location; g) enable payer and health plan specific rules to be documented once and leveraged across client domains (e.g., a plurality of health care providers) and platforms without additional build or translation; and h) submit the electronic plan to the correct health plan, as indicated in the electronic eligibility response. Any one of these features may increase the likelihood that a claim is generated accurately and will be adjudicated without error.

Accordingly, in one aspect, an embodiment is directed to one or more computer storage media having computer-executable instructions embodied thereon that, when executed by a computer, causes the computer to perform operations. The operations include receiving scan data corresponding to an insurance card. The scan data comprises an identification of a payer and an identification of a health plan of the payer. The operations also include receiving transaction data from electronic data interchange (EDI) insurance transactions. The transaction data comprises data corresponding to a plurality of employers, a plurality of payers, and a plurality of health plans provided by the plurality of payers. The operations further include training a machine learning model with the transaction data to build a mapping of the plurality of employers, the plurality of payers contracted with each employer of the plurality of employers, and the plurality of health plans provided by the plurality of payers for each employer of the plurality of employers. The operations may also include, utilizing the machine learning model, verifying the scan data is mapped in accordance with the mapping.

In another aspect of the invention, an embodiment of the present invention is directed to a computerized method. The method includes receiving transaction data from electronic data interchange (EDI) insurance transactions. The transaction data comprises data corresponding to a plurality of employers, a plurality of payers, and a plurality of health plans provided by the plurality of payers. The method also includes training a machine learning model with the transaction data to build a mapping of the plurality of employers, the plurality of payers contracted with each employer of the plurality of employers, and the plurality of health plans provided by the plurality of payers for each employer of the plurality of employers.

In a further aspect, an embodiment is directed to a computerized system that includes one or more processors and a non-transitory computer storage medium storing computer-useable instructions that, when used by the one or more processors, cause the one or more processors to: receive scan data corresponding to an insurance card, the scan data comprising an identification of a payer and an identification of a health plan of the payer; and utilize a machine learning model trained to build a mapping of the plurality of employers, the plurality of payers contracted with each employer of the plurality of employers, and the plurality of health plans provided by the plurality of payers for each employer of the plurality of employers to verify the scan data is mapped in accordance with the mapping.

An exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other purpose computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of computer-readable media. Computer-readable media can be any available media that might be accessed by control server 102, and includes volatile and nonvolatile media, as well as removable and nonremovable media. By way of example, and not limitation, computer-readable media may comprise computer storage media and communication media. Computer storage media includes both volatile and nonvolatile, removable and nonremovable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, ambulatory settings, medical billing and financial offices, hospital administration settings, home healthcare environments, clinicians' offices, Center for Disease Control, Centers for Medicare & Medicaid Services, World Health Organization, any governing body either foreign or domestic, Health Information Exchange, and any healthcare/government regulatory bodies not otherwise mentioned. Clinicians may comprise a treating physician or physicians; specialists such as intensivists, surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
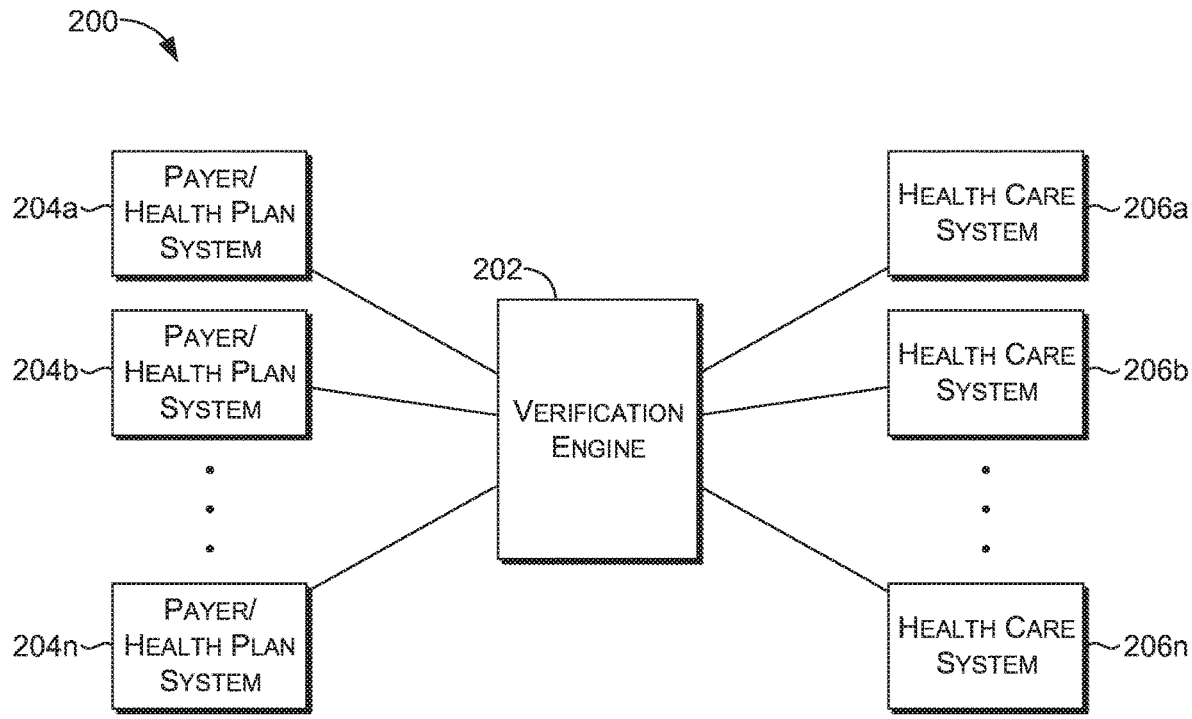
FIG. 2 is a block diagram of an exemplary system for intelligently linking payer/health plan combinations to specific employers, in accordance with an embodiment of the present invention.

Turning now to FIG. 2, an exemplary linking and verification system 200 is depicted suitable for use in implementing embodiments of the present invention. The linking and verification system 200 is merely an example of one suitable computing system environment and is not intended to suggest any limitation as to the scope of use or functionality of embodiments of the present invention. Neither should the linking and verification system 200 be interpreted as having any dependency or requirement related to any single module/component or combination of modules/components illustrated therein.

The linking and verification system 200 includes verification engine 202, payer/health plan system(s) 204a-204n, and health care system(s) 206a-206n all m communication with one another via a network. The network may include, without limitation, one or more secure local area networks (LANs) or wide area networks (WANs). The network may be a secure network associated with a facility such as a healthcare facility. The secure network may require that a user log in and be authenticated in order to send and/or receive information over the network.

The components/modules illustrated in FIG. 2 are exemplary in nature and in number and should not be construed as limiting. Any number of components/modules may be employed to achieve the desired functionality within the scope of embodiments hereof. Further, components/modules may be located on any number of servers. By way of example only, verification engine 202, payer/health plan system(s) 204a-204n, and health care system(s) 206a-206n might reside on a server, cluster of servers, or a computing device remote from one or more of the remaining components. Although illustrated as separate systems, verification engine 202, payer/health plan system(s) 204a-204n, and health care system(s) 206a-206n, the functionality provided by each of these components might be provided as a single component/module. For example, components of the verification engine 202 might reside on a payer/health plan system or a health care system. The single unit depictions are meant for clarity, not to limit the scope of embodiments in any form.

Components of the linking and verification system 200 may include a processing unit, internal system memory, and a suitable system bus for coupling various system components, including one or more data stores for storing information (e.g., files and metadata associated therewith). Components of the linking and verification system 200 typically includes, or has access to, a variety of computer-readable media.

It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components/modules, and in any suitable combination and location. Various functions described herein as being performed by one or more entities may be carried out by hardware, firmware, and/or software. For instance, various functions may be carried out by a processor executing instructions stored in memory.

Verification engine 202 generally receives transaction data (e.g., EDI insurance transactions) from payer/health plan system(s) 204a-204n and health care system(s) 206a-206n and trains a machine learning model to build a mapping of a plurality of employers, a plurality of payers contracted with each employer of the plurality of employers, and a plurality of health plans provided by the plurality of payers for each employer of the plurality of employers. For clarity, EDI insurance transactions may include eligibility, claim, claim status, and remittance transactions. The machine learning model can be utilized to verify insurance (e.g., payer/health plan combination) for a patient that presents an insurance card or predict insurance for a patient that does not present an insurance card.

Each of payer/health plan system(s) 204a-204n generally facilitates the exchange of EDI insurance transactions between health care system(s) 206a-206n and a payer. For example, the payer/health plan system(s) 204a-204n may receive transactions corresponding to claims and encounter information, payment and remittance advice, claims status, eligibility, enrollment and disenrollment, referrals and authorizations, coordination of benefits, and premium payments. Each of these transactions may be utilized to facilitate medical claim data verification. Moreover, each of these transactions may be utilized by verification engine 202 to verify and/or predict payer/health plan combinations.

One or more of the health care system(s) 206a-206n includes or has access to infrastructure that is capable of storing electronic health records (EHRs) of patients associated with health care system(s) 206a-206n. EHRs may comprise electronic clinical documents such as images, clinical notes, orders, summaries, reports, analyses, or other types of electronic medical documentation relevant to a particular patient's condition and/or treatment. Electronic clinical documents contain various types of information relevant to the condition and/or treatment of a particular patient and can include information relating to, for example, patient identification information, insurance (e.g., payer/health plan) information, employer information, work location, images, alert history, culture results, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, and a host of other relevant clinical information. In some embodiments, health care system(s) 206a-206n may receive data from health information exchanges ("HIEs"), personal health records ("PHRs"), patient claims, and other health records associated with a patient. These electronic health records contain many different types of data in many different formats (e.g., non-standard formats) that are stored in separate locations. This makes the data very difficult to use and understand in its original format, and difficult to find any particular type of data. In one embodiment, selected data used by the present system may be extracted and converted into a standard format making the data easier to manage, access and incorporate into the components of the present system including the present machine learning model.

User device (not shown in FIG. 2) may be any type of computing device used within a healthcare facility or as part of the claims processing process to receive, display, and send information to another user or system. The user device may be capable of communicating via the network with verification engine 202, payer/health plan system(s) 204a-204n, or health care system(s) 206a-206n. Such devices may include any type of mobile and portable devices including cellular telephones, personal digital assistants, tablet PCs, smart phones, and the like.

User device is configured to display information to a user via a series of user interfaces. For example, the user interface may include information corresponding to scan data of an insurance card such as an identity of a payer and a health plan of the payer. Additionally, or alternatively, in some embodiments, the scan data comprises an identification of an employer. The user interface may enable a user to review or revise scan data that has been automatically extracted by a card scanning service into appropriate fields of the user interface prior to saving the scan data in an electronic health record of a patient. Additionally, the user interface may provide a display of a front image capture and a back image capture of the insurance card. The user interface may provide employer and work location address information imported from a registration system or an EHR. A filtered list of valid payer/health plan combinations for specific employers may also be provided by the user interface. Embodiments are not intended to be limited to visual display but rather may also include audio presentation, visual presentation, combined audio/visual presentation, and the like.

In practice, a patient may present an insurance card to a facility associated with a health care system 206a-206n. The insurance card is scanned and scan data is communicated to verification engine 202. The scan data may include an identification of a payer and an identification of a health plan of the payer. Additionally, or alternatively, in some embodiments, the scan data comprises an identification of an employer. At the same time, the verification engine 202 has been receiving transaction data from EDI insurance transactions. The transaction data comprises data corresponding to a plurality of employers, a plurality of payers, and a plurality of health plans provided by the plurality of payers. The verification engine 202 trains a machine learning model with the transaction data and builds a mapping of the plurality of employers, the plurality of payers contracted with each employer of the plurality of employers, and the plurality of health plans provided by the plurality of payers for each employer of the plurality of employers. Utilizing the trained model, the verification engine 202 can verify the scan data is mapped appropriately and the proper payer/health plan combination is saved to the EHR for the patient.

Alternatively, if the patient fails to provide an insurance card (e.g., initial health plan identification data is missing that does not identify the correct payer/health plan combination assigned to the patient), the trained model can be utilized by the verification engine 202 to predict the payer/health plan combination for the patient. Moreover, as the verification engine 202 receives additional data from the payer/health plan system 204a-204n and/or the health care system 206a-206n, the machine learning model is continuously updated to provide accurate and up-to-date verifications and predictions.

Figure 3:
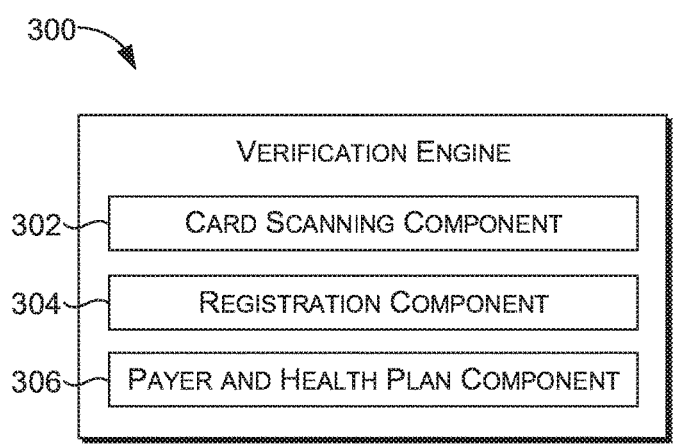
FIG. 3 is a block diagram of an exemplary verification engine, in accordance with an embodiment of the present invention.

In FIG. 3, an exemplary verification engine 300 (such as verification engine 202 of FIG. 2) is depicted suitable for use in implementing embodiments of the present invention. As described above, the verification engine 300 generally receives transaction data (e.g., EDI insurance transactions) from a payer/health plan system (such as payer/health plan system(s) 204a-204n of FIG. 2) and health care system (such as health care system(s) 206a-206n of FIG. 2) and trains a machine learning model to build a mapping of a plurality of employers, a plurality of payers contracted with each employer of the plurality of employers, and a plurality of health plans provided by the plurality of payers for each employer of the plurality of employers. The machine learning model can be utilized to verify insurance (e.g., payer/health plan combination) for a patient that presents an insurance card or predict insurance for a patient that does not present an insurance card.

As illustrated in FIG. 3, the verification engine 300 includes card scanning component 302, registration component 304, and payer and health plan component 306.

The card scanning component 302 generally receives scan data corresponding to an insurance card. The scan data comprises an identification of a payer and an identification of a health plan of the payer. Additionally, or alternatively, in some embodiments, the scan data comprises an identification of an employer. Optical character recognition (OCR) may be utilized by the card scanning component to automatically extract data from the insurance card into appropriate text fields.

The registration component 304 generally provides a user interface that enables a user to view the front and back of the card image capture, review OCR field capture, and manually correct any information prior to saving the scan data to the EHR. Additionally, the registration component 304 may provide a user interface that enables a user to view employer and work location address information important from a registration system of a health care system or manually enter the employer name and work location address information. In some embodiments, the registration component 304 provides a user interface that generates a filtered list of valid payer/health plan combinations for a specific employer on a GUI, such as when a patient does not present an insurance card, or does not provide and input requested plan identifiers to the system. Upon generating the filtered list of valid payer/heath plan combinations, the GUI allows a user to select the appropriate plan.

The payer and health plan component 306 generally receives, verifies or predicts insurance information. To do so, the payer and health plan component 306 initially utilizes the payer name from the insurance card to capture a payer display name. The health plan name from the insurance card is also utilized to capture a health plan display name. Using X12N 271 eligibility responses, the payer and health plan component 306 records payer's name and payer's identification from transactions (e.g., NM1*PR*2*ABC COMPANY*****PI*842610001~, where ABC COMPANY is the payer's name and 842610001 is the payer's identification). The X12N 271 eligibility responses can also be utilized to capture plan begin and plan end dates (e.g., DTP*346*D8*20060101~). The payer and health plan component 306 verifies payers that have name and identification and valid begin plan dates. Verified payers are provided with a system-generated unique payer identification.

The payer and health plan component 306 utilizes X12N 271 eligibility responses to record insurance type codes and the plan coverage description (e.g., EB*B**1^33^35^47^86^88^98^AL^MH^UC*HM*GOLD 123 PLAN*27*10*****Y~, where HM is the insurance type code and GOLD 123 is the plan coverage description). Receipt of paid X12N 835 remittances are utilized to confirm valid payer name and plan coverage name (description) combinations. Health plans with insurance type codes and plan coverage descriptions with valid plan dates are verified and have a system generated unique health plan identification.

Figure 4:
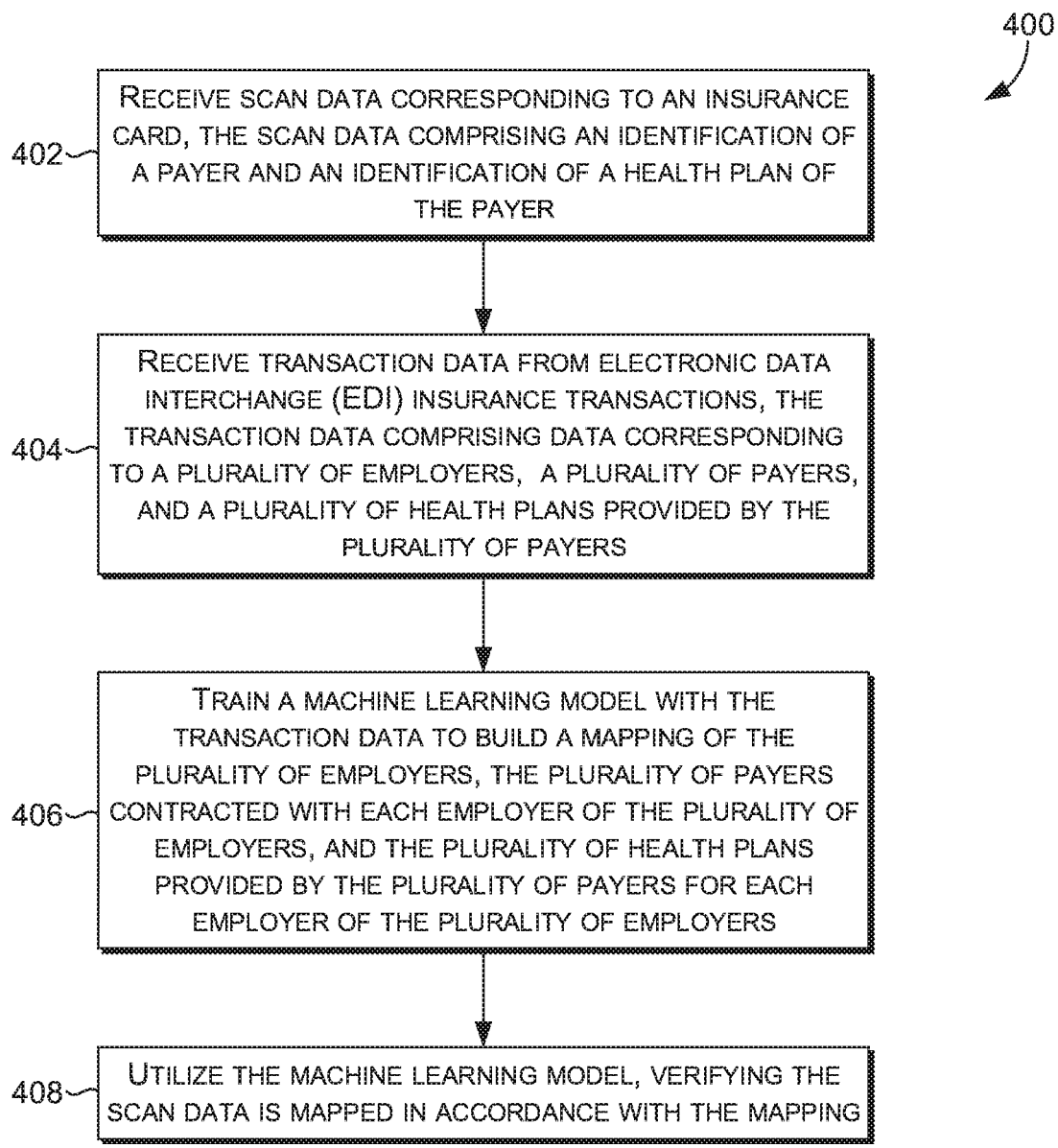
FIG. 4 is a flow diagram showing an exemplary method utilizing a machine learning model to verify payers and health plans, in accordance with various embodiments of the present invention.

Turning now to FIG. 4, a flow diagram is provided illustrating a method 400 for training and utilizing a machine learning model to verify payers and health plans, in accordance with an embodiment of the present invention. Method 400 may be performed by any computing device (such as computing device described with respect to FIG. 1) with access to a linking and verification system (such as the one described with respect to FIG. 2) or by one or more components of the linking and verification system (such as components of the verification engine described with respect to FIG. 3).

Initially, as shown at step 402, scan data corresponding to an insurance card is received. The scan data comprises an identification of a payer and an identification of a health plan of the payer. Additionally, or alternatively, in some embodiments, the scan data comprises an identification of an employer.

At step 404, transaction data is received from EDI insurance transactions. The transaction data comprises data corresponding to a plurality of employers, a plurality of payers, and a plurality of health plans provided by the plurality of payers.

At step 406, a machine learning model is trained with the transaction data to build a mapping of the plurality of employers, the plurality of payers contracted with each employer of the plurality of employers, and the plurality of health plans provided by the plurality of payers for each employer of the plurality of employers. For example, each mapping includes at least three components mapped together to define a valid combination of employer-payer-health plan. For a particular "employer" value/name, there may be many different combinations of payer-health plan combinations. Other data associated with a health plan may also be mapped to a combination.

At step 408, the machine learning model is utilized to verify the scan data includes a valid combination of employer-payer-health plan in accordance with the mapping.

In some embodiments, a user interface is provided that displays fields for the identification of the payer, the identification of the health plan of the payer, and the identification of the employer. A card scanning service may automatically extract the scan data into appropriate fields of the user interface. The extracted scan data may comprise the identification of the payer, the identification of the health plan of the payer, and the identification of the employer. The user interface enables a user to review or revise the extracted scan data prior to saving the scan data in an electronic health record of a patient.

The user interface may also provide a view of a front image capture and a view of a back image capture of the insurance card. Additionally, the user interface may provide a view of employer and work location address information that has been imported from a registration system or an EHR. In some embodiments, the user interface displays a filtered list of valid payer/health plan combinations for specific employers. The user is enabled to select, via the user interface, a payer/health plan combination for a patient from the filtered list of valid payer/health plan combinations. For example, if the patient does not present an insurance card (or other appropriate input data about a health plan) but provides employer and work location information, the system may be able to predict payer/health plan combinations that are likely to have the patient enrolled based on the input data of employer and work location.

Figure 5:
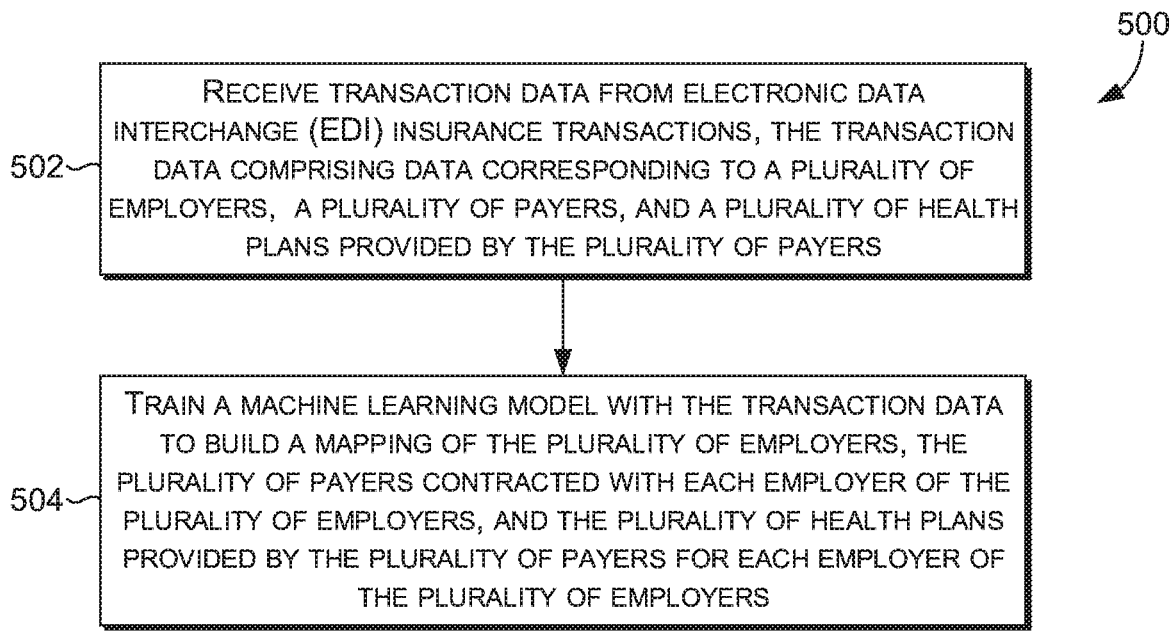
FIG. 5 is a flow diagram showing an exemplary method for training a machine learning model to verify payers and health plans, in accordance with various embodiments of the present invention.

Referring now to FIG. 5 a flow diagram is provided illustrating a method 500 for training a machine learning model to verify payers and health plans, in accordance with an embodiment of the present invention. Method 500 may be performed by a computing device (such as computing device described with respect to FIG. 1) with access to a linking and verification system (such as the one described with respect to FIG. 2) or by one or more components of the linking and verification system (such as components of the verification engine described with respect to FIG. 3).

Initially, as shown at step 502, transaction data is received from EDI insurance transactions. The transaction data comprises data corresponding to a plurality of employers, a plurality of payers, and a plurality of health plans provided by the plurality of payers. Data may be extracted from the transactions to identify combinations of employer identifier, payer identifier, and health plan identifier that were verified as valid combinations. Invalid combinations may also be used for training.

At step 504 a machine learning model is trained with the transaction data to build a mapping of the plurality of employer identifiers, the plurality of payer identifiers contracted with each employer of the plurality of employer identifiers, and the plurality of health plan identifiers provided by the plurality of payers for each employer of the plurality of employer identifiers. As stated previously, each mapping includes at least three components mapped together to define a valid combination of employer-payer-health plan. For a particular "employer" identifier/name, there may be many different combinations of payer identifiers mapped to a plurality of health plan identifiers that are valid. The mapping structure is not limited to the example structure since a mapping may be configured in different ways using different computing functions and/or data structures. The ML model may be trained to predict a valid combination based on at least one inputted identifier when other identifiers are missing. For example, the ML model is trained to predict one or more valid payer-health plan combinations when an employer name is provided.

In some embodiments, in response to a patient encounter and/or a request to identify a valid combination, scan data corresponding to an insurance card is received. The scan data may comprise an identification of a payer, and/or an identification of a health plan of the payer. Additionally, or alternatively, in some embodiments, the scan data comprises an identification of an employer. The machine learning model may be utilized to verify the scan data includes a valid combination of identifiers that is mapped in accordance with the mapping. In response to one or more of the identifiers missing from the scan data, the machine learning model generates a predicted set of valid combinations based on the identifiers that were found in the scan data.

In some embodiments, a patient may not have an insurance card (or data is missing from the card) and thus valid data that identifies the employer, payer, and/or health plan is missing. However, the patient may be able to provide an identification of an employer and a work location. The machine learning model may be utilized to predict one or more payer/health plan combinations based on the received identification of the employer and the work location. By inputting an employer name and work location to the machine learning model, the model may predict one or more combinations of valid payer-health plan combinations that are mapped in the system to the inputted employer name based on the inputted employer name corresponding to (matching or closely matching with) the employer identifiers/names that exist in the mappings. The work location data may be used to further identify the employer identifier when multiple names are similar. The predicted combinations may then be displayed on the user interface.

In some embodiments, a user is enabled via a user interface to select a payer/health plan combination of the one or more payer/health plan combinations. The selected payer/health plan combination may be saved in an electronic health record of the patient for generating claim data and/or processing other related transactions. Once a valid combination of payer/health plan is identified, the system may generate claim data based on the valid combination for the patient encounter. The generated claim data may then be transmitted as a transaction, via network communication or other communication channel, to an appropriate third party system that is selected for processing. Since a valid combination of payer/health plan is included in the claim data, the third party system data records should match and approve the claim data of the transaction. Thus, the present system reduces the amount of transactions being denied and retransmitted.

Figure 6:
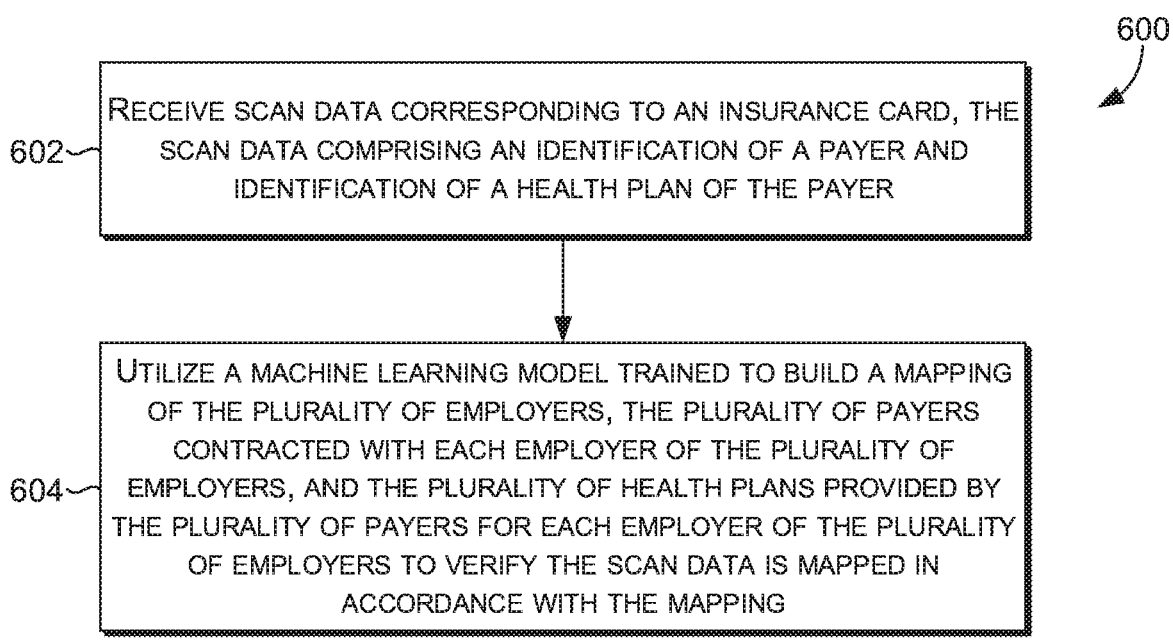
FIG. 6 is a flow diagram showing an exemplary method for utilizing a machine learning model to verify payers and health plans, in accordance with various embodiments of the present invention.

In FIG. 6, a flow diagram illustrates a method 600 for utilizing a machine learning model to verify payers and health plans, in accordance with an embodiment of the present invention. Method 600 may be performed by any computing device (such as computing device described with respect to FIG. 1) with access to a linking and verification system (such as the one described with respect to FIG. 2) or by one or more components of the linking and verification system (such as components of the verification engine described with respect to FIG. 3).

Initially, as shown at step 602, scan data corresponding to an insurance card is received. The scan data comprises an identification of a payer and an identification of a health plan of the payer. Additionally, or alternatively, in some embodiments, the scan data comprises an identification of an employer.

At step 604, a machine learning model that has been trained to build a mapping of a plurality of employers, a plurality of payers contracted with each employer of the plurality of employers, and a plurality of health plans provided by the plurality of payers for each employer of the plurality of employers is utilized to verify the scan data is mapped in accordance with the mapping. Additionally, or alternatively, the machine learning model may be trained to build the mapping based on home addresses and/or physical location of employment of the patients.

The machine learning model may be trained with transaction data received from EDI insurance transactions. The transaction data comprises data corresponding to a plurality of employers, a plurality of payers, and a plurality of health plans provided by the plurality of payers. During training, the machine learning model builds the mapping of the plurality of employers, the plurality of payers contracted with each employer of the plurality of employers, and the plurality of health plans provided by the plurality of payers for each employer of the plurality of employers. As additional information is received, such as notices where claim data is approved or denied in transactions, the machine learning model continues to update the mapping of valid combinations of the plurality of employers, the plurality of payers contracted with each employer of the plurality of employers, and the plurality of health plans provided by the plurality of payers for each employer of the plurality of employers to reflect billing successes and failures. For example, claim data that is approved in a transaction contains a valid combination of employer-payer-health plan identifiers. Conversely, claim data that is denied in a transaction due to, for example, an incorrect or invalid health plan contains an invalid combination of employer-payer-health plan identifiers. This type of feedback may be used to retrain and/or update the machine learning model.

In some embodiments, a user interface is provided that displays fields for the identification of the payer, the identification of the health plan of the payer, and the identification of the employer. The scan data may automatically be extracted by a card scanning service into appropriate fields of the user interface. The user interface enables a user to review or revise the extracted scan data prior to saving the scan data in an electronic health record.

As can be understood, the present invention provides systems, methods, and user interfaces for training and utilizing a machine learning model to verify payers and health plans. The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated and within the scope of the claims.

What is claimed is:

1. A non-transitory computer-readable medium storing computer-executable instructions that, when executed by a computer including a processor, cause the computer to perform functions comprising:
   training a machine learning model to predict a payer-health plan combination in response to missing data by:
      receiving transaction data from electronic data interchange (EDI) insurance transactions, the transaction data comprising data corresponding to a plurality of employers, a plurality of payers contracted with one or more employers of the plurality of employers, and a plurality of health plans provided by the plurality of payers for one or more employers of the plurality of employers;
      extracting features from the received transaction data that identify combinations of employer identifier, payer identifier, and health plan identifier that are valid combinations of health plans; and
      training the machine learning model to predict a payer-health plan combination by inputting the valid combinations of employer identifier, payer identifier, and health plan identifier to the machine learning model;
   in response to a request to identify a valid combination, obtaining employer and work location data associated with a patient who does not present an insurance card;
   inputting the employer and work location data into the machine learning model; and
   generating, by the machine learning model, and displaying on a display, a predicted set of one or more payer-health plan combinations that are valid with an employer identifier that corresponds to the employer and work location data that is inputted.

2. The non-transitory computer-readable medium of claim 1, further comprising instructions that, when executed by at least the processor, cause the processor to:
   provide a user interface that displays fields for an identification of the payer, an identification of the health plan of the payer, and an identification of the employer.

3. The non-transitory computer-readable medium of claim 2, further comprising instructions that, when executed by at least the processor, cause the processor to:
   automatically extract, at a card scanning service, scan data into appropriate fields of the user interface, the scan data corresponding to an insurance card and comprising the identification of a payer and the identification of a health plan of the payer.

4. The non-transitory computer-readable medium of claim 3, further comprising instructions that, when executed by at least the processor, cause the processor to:
   enable a user, via the user interface, to review or revise the extracted scan data prior to saving the extracted scan data in an electronic health record of a patient.

5. The non-transitory computer-readable medium of claim 3, wherein the extracted scan data comprises the identification of the payer, the identification of the health plan of the payer, and the identification of the employer.

6. The non-transitory computer-readable medium of claim 3, further comprising instructions that, when executed by at least the processor, cause the processor to:
display, at the user interface, a view of a front image capture and a view of a back image capture of the insurance card.

7. The non-transitory computer-readable medium of claim 1, further comprising instructions that, when executed by at least the processor, cause the processor to:
display, on a user interface, the employer and work location data imported from a registration system.

8. The non-transitory computer-readable medium of claim 1, further comprising instructions that, when executed by at least the processor, cause the processor to:
display, on a user interface, a filtered list of the valid payer/health plan combinations based on the inputted employer and work location data.

9. The non-transitory computer-readable medium of claim 8, further comprising instructions that, when executed by at least the processor, cause the processor to:
enable, via the user interface, a user to select a payer/health plan combination for a patient.

10. A method for predicting a payer/health plan combination for a patient comprising:
training a machine learning model to predict valid combinations of employer-payer-health plan in response to one or more missing identifiers by:
receiving transaction data from electronic data interchange (EDI) insurance transactions, the transaction data comprising data corresponding to valid combinations of a plurality of employers, a plurality of payers contracted with each employer of the plurality of employers, and a plurality of health plans provided by the plurality of payers for each employer of the plurality of employers;
extracting features from the received transaction data that identify combinations of employer identifier, payer identifier, and health plan identifier that are valid combinations; and
training a machine learning model to predict valid combinations for a patient by inputting the valid combinations of employer identifier, payer identifier, and health plan identifier to the machine learning model;
in response to a request to identify a valid combination based on at least one missing identifier, obtaining one known identifier corresponding to an employer name, a payer name, or a health plan name, and obtaining work location data associated with a patient wherein the other identifiers are missing;
inputting the one known identifier and the work location data into the machine learning model; and
generating, by the machine learning model, and displaying on a user interface, a predicted set of one or more valid combinations of employer-payer-health plans that correspond to the inputted one known identifier and the work location information,
wherein each combination from the predicted set is selectable via the user interface.

11. The method of claim 10, further comprising:
generating claim data for a patient encounter based on a selected valid combination from the user interface; and
transmitting the generated claim data as a transaction, via network communication or other communication channel, to a selected third party system for processing.

12. The method of claim 10, wherein the method further comprises:
utilizing the machine learning model to verify that a selected combination from the predicted set is mapped in accordance with the mapping.

13. The method of claim 10, wherein obtaining the one known identifier comprises:
receiving an identification of an employer name and a work location.

14. The method of claim 13, wherein the method further comprises:
predicting, by the machine learning model, the predicted set of one or more valid combinations including one or more payer/health plan combinations based on the identification of the employer and the work location.

15. The method of claim 14, wherein the method further comprises:
enabling a user, via the user interface, to select a payer/health plan combination of the one or more payer/health plan combinations.

16. The method of claim 15, wherein the method further comprises:
saving the selected payer/health plan combination in an electronic health record of a patient.

17. A system comprising:
one or more processors; and
a non-transitory computer storage media storing computer-useable instructions that, when used by the one or more processors, cause the one or more processors to:
train a machine learning model to predict a payer-health plan combination for a patient in response to missing data by:
receiving transaction data from electronic data interchange (EDI) insurance transactions, the transaction data comprising data corresponding to a plurality of employers, a plurality of payers contracted with each employer of the plurality of employers, and a plurality of health plans provided by the plurality of payers for each employer of the plurality of employers;
extracting features from the received transaction data that identify combinations of employer identifier, payer identifier, and health plan identifier that are valid combinations; and
training the machine learning model to predict a payer-health plan combination for a patient by inputting the valid combinations of employer identifier, payer identifier, and health plan identifier to the machine learning model;
in response to a request to identify a valid combination when payer and health plan identifiers are missing, obtain employer and work location data associated with a patient who does not present an insurance card;
input the employer and work location data into the machine learning model; and
generate, by the machine learning model, a predicted set of one or more payer-health plan combinations that are valid with an employer identifier that corresponds to the inputted employer and work location information.

18. The system of claim 17, wherein the system is further configured to:
receive additional transaction data from the EDI insurance transactions, the additional transaction data comprising (i) approvals of claim data containing valid combinations of employer-payer-health plan identifiers and (ii) denials of claim data containing invalid combinations of employer-payer-health plan identifiers;

extract a dataset of features from the additional transaction data corresponding to the approvals and the denials; and retrain the machine learning model based on the approvals and denials.

19. The system of claim 17, wherein the system is further configured to:

generate claim data for a patient encounter based on a selected valid combination from the user interface; and transmit the generated claim data as an electronic transaction, via network communication or other communication channel, to a selected third party system for processing.

20. The system of claim 17, wherein the computer-executable instructions are further configured to cause the at least one or more processors to:

provide a user interface that displays fields for an identification of the payer, an identification of the health plan of the payer, and an identification of the employer;

automatically extract, at a card scanning service, scan data into appropriate fields of the user interface, the scan data corresponding to an insurance card and comprising the identification of the payer and the identification of the health plan of the payer; and enable, via the user interface, a review or a revision of the extracted scan data prior to saving the extracted scan data in an electronic health record.

* * * * *